United States Patent

Hermann

[11] Patent Number: 5,984,928
[45] Date of Patent: Nov. 16, 1999

[54] CLAMPING ARRANGEMENTS FOR AN ORTHOPEDIC FIXATION DEVICE AND USE THEREOF

[76] Inventor: Werner Hermann, Keltenweg 6, CH - 6312, Steinhausen, Switzerland

[21] Appl. No.: 09/109,079

[22] Filed: Jul. 2, 1998

[51] Int. Cl.$^6$ ................................................. A61B 17/70
[52] U.S. Cl. .............................................. 606/72; 606/61
[58] Field of Search .................................. 606/61, 60, 72, 606/73; 623/17

[56] References Cited

U.S. PATENT DOCUMENTS

| | | | |
|---|---|---|---|
| 5,487,744 | 1/1996 | Howland | 606/61 |
| 5,667,507 | 9/1997 | Corin et al. | 606/61 |
| 5,738,685 | 4/1998 | Halm et al. | 606/61 |
| 5,752,955 | 5/1998 | Errico et al. | 606/61 |

*Primary Examiner*—Michael Buiz
*Assistant Examiner*—Jonathan Goldberg
*Attorney, Agent, or Firm*—Browdy and Neimark

[57] ABSTRACT

The clamping arrangement (1, 6) comprises a clamping body (6) and an implant pin (1) fastened therein. The clamping body (6) has a recess (7) for receiving the implant pin (1) and a slit (10), starting at the recess (7), by means of which two clamping jaws (8, 9) are formed which, when pressed together, cause the fastening of the implant pin (1). The slit (10) is arranged in such a way that its imagined extension contains the longitudinal axis of the implant pin (1). To reduce material fatigue and wear, either the outer surface of the implant pin (1) or the wall of the recess (7) have set-back areas (6.7, 6.8), which do not touch the surface respectively located opposite them. With suitable embodiment and arrangement, the set-back areas and the relief recesses (1.3, 1.4, 6.3, 6.4) can be created in the same step, in particular by means of a screw thread or several channels in the implant pin (1) or the recess (7). To prevent nicking effects at the exit cross sections of the implant pin (1) from the clamping body (6), either the areas of these exit cross sections of the implant pin (1), or the areas of the end cross sections of the recess (7) have relief recesses (1.3, 1.4, 6.3, 6.4). The clamping arrangement (1, 6) is employed as part of an internal or external fixation device for orthopedic or traumatologic treatments.

22 Claims, 5 Drawing Sheets

CLAMPING ARRANGEMENTS FOR AN ORTHOPEDIC FIXATION DEVICE AND USE THEREOF

FIELD OF THE INVENTION

The invention relates to clamping arrangements for an orthopedic fixation device, having an implant pin which can be fixed in place in a bone, and a clamping body, which has a recess connecting two oppositely located exterior surfaces of the clamping body and receives the implant pin, and a slit starting at the recess, whose imagined extension contains the longitudinal axis of the recess and by means of which two resilient clamping jaws are formed on the clamping body which, when they are clamped together, fastens the implant pin on the clamping body. The invention further relates to the use of these clamping arrangements in connection with an internal and/or external fixation device.

BACKGROUND OF THE INVENTION

Clamping devices of this type are used in orthopedics and traumatology for various purposes as components of internal or external fixation devices. For example, Swiss Patent Application 00186/96 describes an internal fixation device which is used in case of morbid changes, such as spondylosis at vertebrae and disks, wherein the position of the vertebrae is corrected and the relative position of the affected vertebrae caused by the correction is fixed in place.

A fixation device of the type mentioned at the outset basically consists of an implant pin which is fastened in a bone. Generally pins with a thread, i.e. screws, are used as implant pins, which are screwed into a prepared bore in the bone. The portion of the implant pin outside of the bone protrudes through a first recess, or respectively bore of a clamping body. Within the scope of the instant description, the term "clamping arrangement" should be understood as being the clamping body and the implant pin fastened therein. The clamping body has a second bore which is oriented transversely in respect to the first bore and in which a clamping screw is received. A slit starting at the first bore and extending perpendicularly in respect to the longitudinal axis of the clamping screw forms two resilient clamping jaws on the clamping body. The slit is arranged in such a way that its imagined extension contains the longitudinal axis of the implant pin. The clamping screw is used for clamping the clamping jaws together and in the process to fix the implant pin in place in the clamping body. The head of the clamping screw is designed in such a way that it can receive a connecting rod, which also extends through respective heads of clamping screws of one or several more fixation devices, wherein the connecting rod can be straight or curved, depending on the requirements. With internal fixation devices, all above described components are inside the body of the person with the implant, while with external fixation devices only a portion of the implant pin is arranged in the body of the person with the implant, while the remainder of the implant pin protrudes out of the body, so that the clamping body and the connecting rod are located outside the body of the person with the implant.

In the course of movements of the person with the implant, the implant pin and the clamping body also move, which can also cause relative movements between the implant pin and the clamping body. Regardless of whether these are linear movements in the direction of the axis of the implant pin or rotations of the implant pin or bending of the implant pin, these relative movements are always minute movements. The forces transferred in the course of the relative movements between the implant pin and the clamping body not only result in mechanical wear indications on the surface, caused by friction, but mainly also, since these are alternating stresses, in fatigue of the material, which has a negative effect on the service life of the clamping arrangement. This undesired effect not only occurs in the cross sections where the implant pin exits the clamping body, but at the entire contact surface between the implant pin and the clamping body. Material fatigue in particular results in the formation of fine cracks, which has a particularly disadvantageous effect on the implant pin as the mechanically weaker component. If stress peaks occur over time because of particular movements of the person with the implant, larger cracks extending from the fatigue cracks can form, from which overload breakage can develop in the end. As already mentioned, it is also disadvantageous that rubbed off particles are created from the frictional forces between the surface of the implant pin and the wall of the recess in the clamping body, which are also a sign of undesirable wear and which, in the case of internal fixation devices, can lead to metallosis in the case of internal fixation devices. Although generally implants are made of materials which are physiologically well tolerated, this applies only to particles of macroscopic size, while microscopic elements, such as rubbed-off particles made of the same materials are physiologically not tolerated and can result in the metallosis mentioned.

OBJECT AND SUMMARY OF THE INVENTION

It is therefore the object of the invention to improve a clamping arrangement of the type mentioned at the outset in such a way, that the mentioned disadvantages do not occur.

Accordingly, it is provided in accordance with the invention that either the outer surface of the implant pin or the inner surface of the recess are not cylindrically designed and instead have set-back areas, because of which the remaining areas located on the originally cylindrical surface appear as protrusions, so to speak, whose culmination areas touch the respectively oppositely located surface areas. In this case the guidance of the implant pin is still provided over the entire length of the recess of the clamping body. However, minute movements, in particular in the axial direction, are possible with reduced friction effects. Wear is reduced by this. The reason for a reduced formation of fatigue cracks is to be seen in that the protrusions of the one surface which touch the other surface have a certain amount of elasticity and are slightly elastically deformed by the forces acting during the relative movement, so that locally the relative movements and therefore the appearance of fatigue effects in the material based on alternating stress are prevented or at least greatly reduced, which has the result of the service life of the clamping device being increased. At the same time the formation of rubbed-off particles over time is reduced. Although the reduction of rubbed-off particles is generally desired, it is particularly necessary in connection with the fixation devices with an increased service life in accordance with the invention. With otherwise equal design of the components, the amount of rubbed-off particles does increase with the length of time of use. It is therefore advantageous in connection with implants with a long service life, if the amount of rubbed-off material produced over time is small, so that the total amount of rubbed-off material during the time the implant is used does not become too large, so that an increased service life of the implants does not increase the danger of metallosis.

In general the clamping arrangement in accordance with the invention is embodied in such a way that the surface having the set-back areas is the interior surface of the bore, or respectively recess, while the implant pin is designed cylindrically, with the exception of a possible screw thread for screwing it into a bone. Such an embodiment is often preferred, since weakening occurs by creating the set-back areas, which can be more readily accepted in a clamping body than in the implant pin.

However, arranging the set-back areas on the outer surface of the implant pin is also possible and is sometimes preferred, particularly in connection with complicated shapes, since in general outer surfaces can be more easily worked than inner surfaces.

The set-back areas can be created in a simple manner in that the appropriate cylindrical surface is provided with a helically-shaped recess, i.e. basically with a screw thread.

In place of a helically-shaped recess, the set-back areas can also be formed by several channels, or respectively grooves, which preferably extend perpendicularly in relation to the longitudinal axis of the first recess, or respectively of the implant pin.

Regardless of whether the set-back areas are formed by a helical line or several grooves, in detail they can be embodied to be such that the cross section of the helical line, or respectively of the groove, is rounded, trapezoidal, rectangular or dove-tailed-like. In a sectional view containing the longitudinal axis of the recess, or respectively of the implant pin, the set-back areas and the areas of the original cylindrical surface separating them then form a sequence of waves, trapezoids, rectangles or dovetails, wherein preferably a nicking effect is prevented in all transition areas by a suitable rounding.

The above mentioned relative movements between the implant pin and the clamping body which occur in the course of movements of the person with the implant can have unpleasant results, particularly in case of curves in the implant pin. It is obvious that the deformation of the implant pin because of bending is greater than that of the clamping element. Under bending stress within the recess, the implant pin received in the recess would practically not be bent inside the recess, since in that case the clamping element also would have to be correspondingly deformed in the area of the recess, which is the case to only a very limited extent because of the greater bending resistance of the clamping element. In contrast thereto, the implant pin is subjected to increased nicking effects by the edges of the recess in the clamping body at the two exit cross sections where it comes out of the clamping body, which of course also occurs in the form of an alternating stress and results in material fatigue.

It is therefore a further object of the invention to propose a clamping body of the type mentioned at the outset, wherein the stress on the implant pin is reduced, in particular in the exit cross sections.

This further object is attained by the characterizing features of claims 7. Claims 7 to 10 define appropriate exemplary embodiments.

Therefore, in accordance with the invention the outer surfaces of the implant pin in the area of its two exit cross sections, or the inner surface of the recess, or respectively bore, intended for receiving the implant pin are provided with relief recesses in the area of their end cross sections. By means of this it is prevented that in case of bending of the implant pin the latter is pressed against a nicking edge area of the recesses with a small sector of its circumference. In this way it is possible to prevent or reduce the creation of very fine cracks. However, the guide length of the implant pin in the clamping body is reduced, and no reduction of the stress during axial and rotational relative movement occurs.

It should also be mentioned that there is a possibility to apply relief recesses on the implant pin as well as on the clamping body, but the positive effect which can be additionally achieved by this is small.

In an advantageous embodiment of the clamping arrangement, the circular edges at the transition areas from the recess to the outer surfaces of the clamping body are rounded or broken for generating the relief recesses, while the implant pin is not further worked. It is achieved by this step that during bending of the implant pin either no contact with the edge areas occurs, or that no strong pressing occurs against nicking sectors of the edge areas. Because of this the creation of the fine cracks is reduced, with the result that even during occasional tension peaks the danger of breaking is greatly reduced.

In another embodiment of the clamping arrangement the relief recesses are provided on the implant pin, namely in the shape of circumferential grooves at those areas of the latter which contain exit cross sections which, depending on the setting of the fixation device, can lie within a defined area of the implant pin. However, this embodiment has the result, undesirable per se, that the implant pin is weakened in two areas because of the reduction in its diameter. But the weakening can be greatly reduced if the grooves have rounded transition areas. In cases where the implant pin is a screw, the mentioned weakening is of small consequence anyway as long as the diameter of the implant pin in the bottom of the groove is no less than the inner diameter of the screw thread. But such a solution can also require that the diameter of the implant pin be increased.

The arrangement of special relief recesses can be omitted in clamping arrangements in accordance with the invention wherein the implant pin or the recess of the clamping body have recess areas. If appropriately arranged and designed, the helical lines, or respectively the corresponding grooves or channels used for forming the recesses areas, then act themselves as relief recesses in the area of the exit cross sections.

Fixation devices with the clamping arrangements in accordance with the invention can be used in combination with further fixation devices both internally and externally.

The invention will be explained in more detail below by means of several exemplary embodiments, making reference to the drawings.

DETAILED DESCRIPTION OF THE PREFERRED EMBODIMENTS

FIGS. 1 to 10 relate to the prior art as documented by Swiss Patent Application 00186/96.

Figure 1:
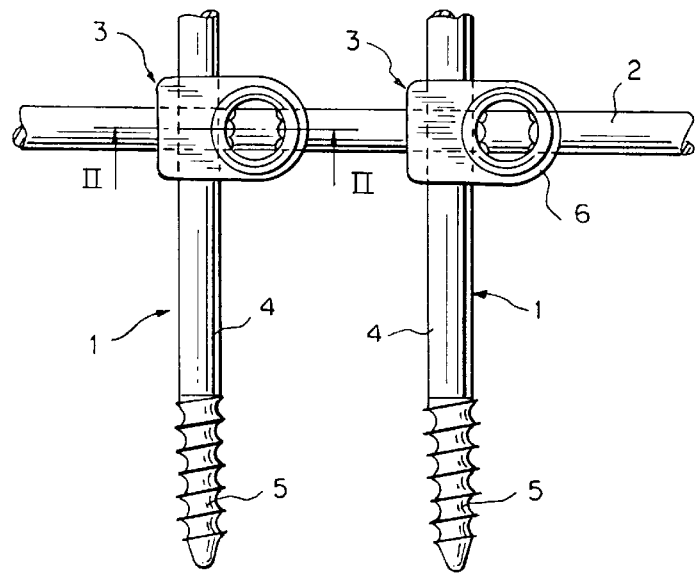
FIG. 1 is a lateral view of a fixation device in accordance with the prior art with two implant pins.
Figure 2:
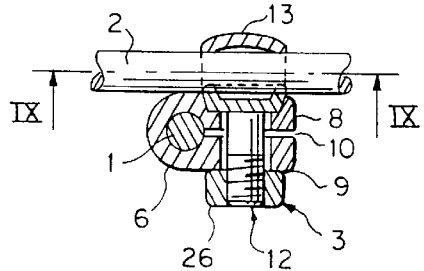
FIG. 2 is a section along the line II—II in FIG. 1.
Figure 2A:
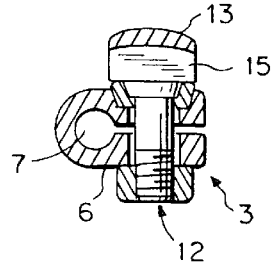
FIG. 2A is a section along line II—II in FIG. 1 without the pin and rod shown in FIG. 1.
Figure 3:
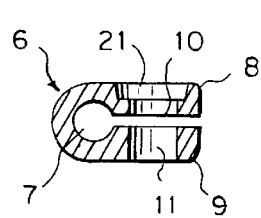
FIG. 3 is a sectional view of a clamping body in accordance with the prior art.
Figure 4:
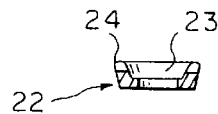
FIG. 4 is a sectional view of a curved washer in accordance with the prior art.
Figure 5:
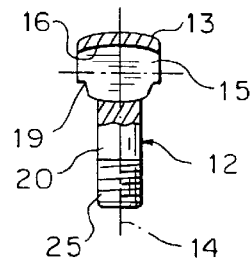
FIG. 5 is a partial sectional view of a clamping screw of the clamping body in accordance with the prior art.
Figure 6:
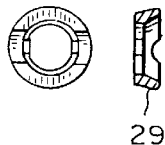
FIG. 6 is a sectional view and a top view of the curved washer in another embodiment in accordance with the prior art.
Figure 7:
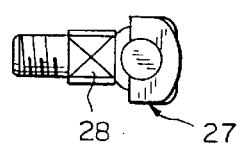
FIG. 7 is a plan view of a clamping screw in another embodiment in accordance with the prior art.
Figure 8:
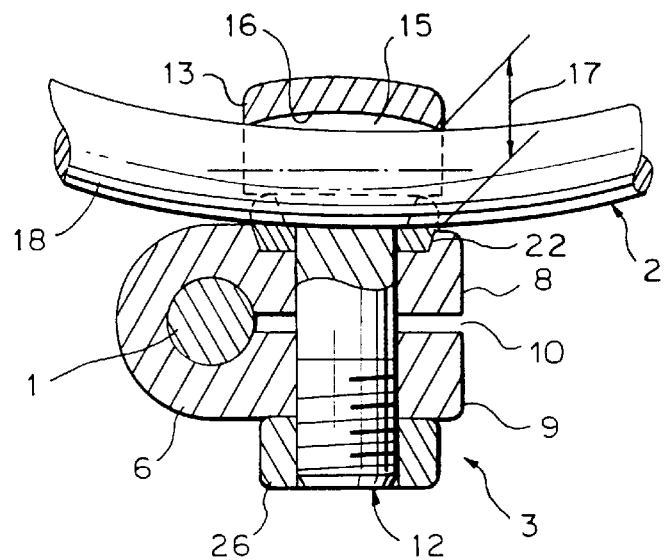
FIG. 8 is a sectional view of a clamping body with an implant pin, a clamping screw, a curved washer and a curved connecting rod on an enlarged scale in accordance with the prior art.
Figure 9:
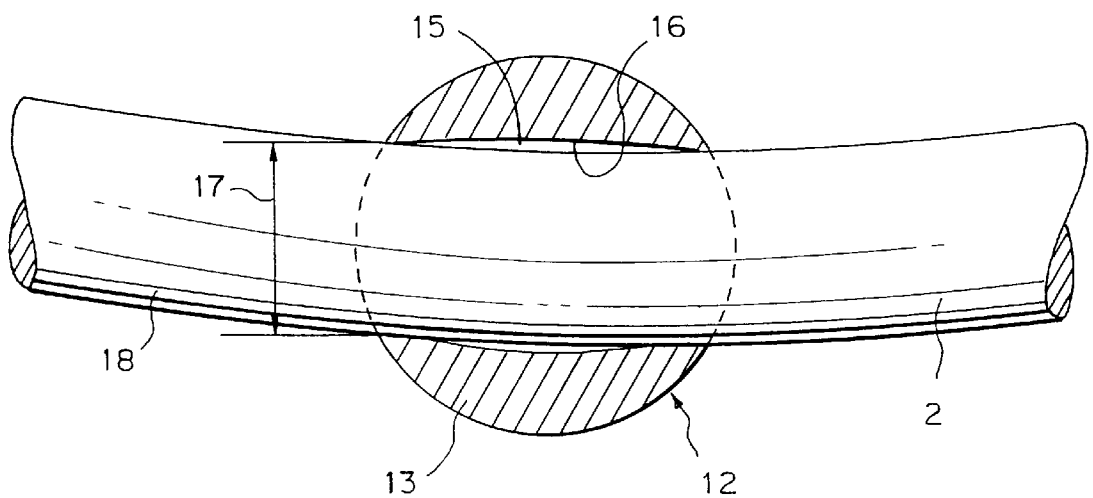
FIG. 9 is a section along the line IX—IX in FIG. 2 on an enlarged scale.
Figure 10:
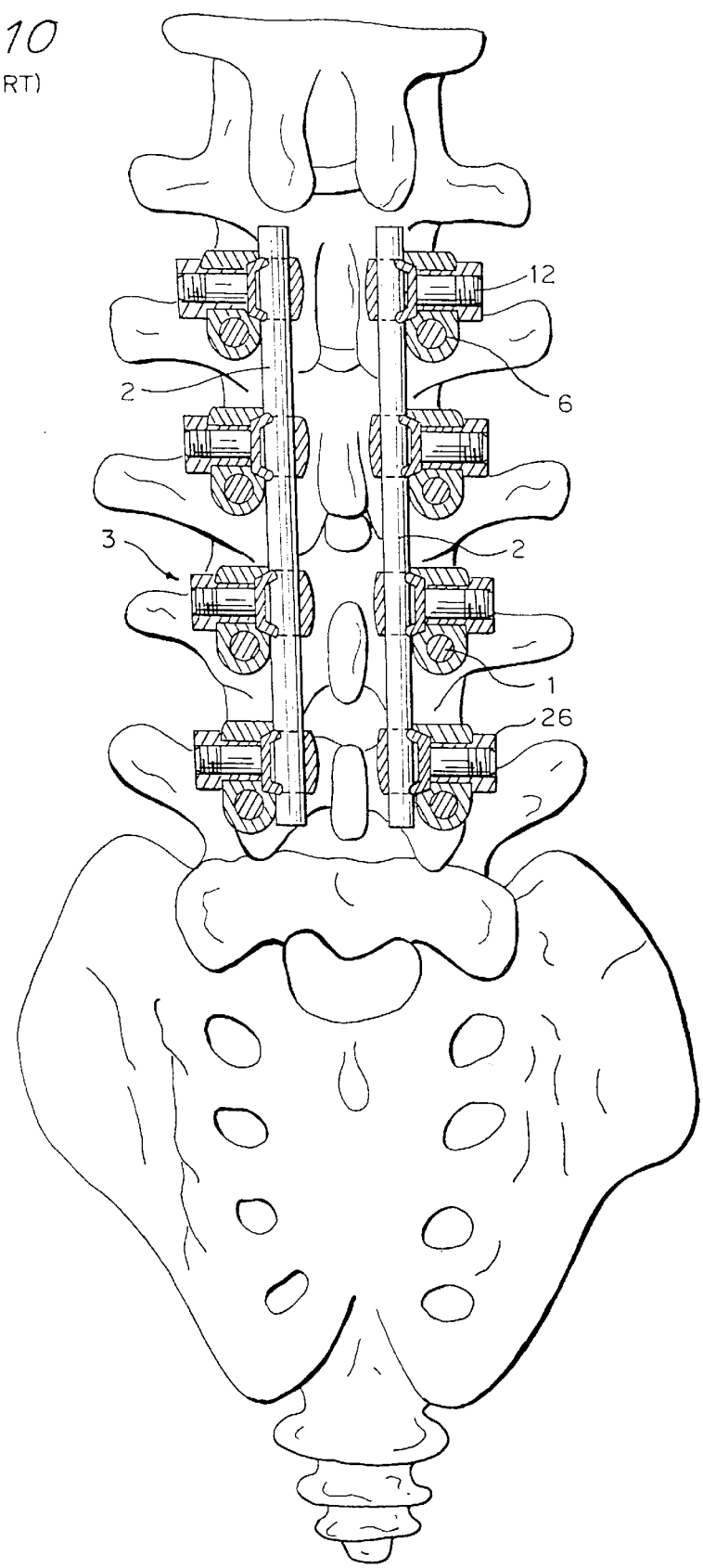
FIG. 10 is a rear view of a portion of a spine with two parallel implant arrangements with respectively four clamping bodies in accordance with the prior art.

Here, implant pins are identified by 1 which, in accordance with FIGS. 1 to 10, are embodied as pedicle screws and are connected with each other by means of a connecting rod 2 and connecting elements 3. The pedicle screws have a shaft 4 and a threaded portion 5, with which they can be screwed into vertebrae 30 as represented in FIG. 10. With such a parallel arrangement it can be advantageous for preventing prestresses in the vertebrae to employ pedicle screws with opposite screw threads. The connecting elements 3 consist of a clamping body 6, which has a first recess, or respectively bore 7 for receiving a pedicle screw 1, and a slit 10, connected with the first bore 7 and constituting two resilient clamping jaws 8, 9. A second bore 11, which crosses the first bore 7 and extends perpendicularly in relation to the slit 10, is provided in the clamping jaws 8, 9 for receiving a clamping screw 12 of the connecting element 3. A bore 15 for guiding and holding the connecting rod 2 and extending perpendicularly in relation to the longitudinal axis 14 of the clamping screw 12, is arranged in a head 13 of the clamping screw 12. The surface 16 of the bore 15 is curved toward the inside and the outside, so that the diameter 17 of the bore 15 at its ends approximately corresponds to the diameter of the connecting rod 2 and the curvature is, for example, circular or ellipsoidal. It is possible to guide and hold a straight as well as a curved element 18 of a connecting rod 2, which has been individually adapted to the curvature of the spine, in a bore 15 embodied in this way, wherein the connecting rod 2 rests linearly on both ends of the bore 15, as represented in FIGS. 8 and 9. A transition area 19 between the head 13 and a shaft 20 of the clamping screw 12 is conically designed, wherein the bore 15 partially extends in the conical transition area 19.

A conical depression 21, in which a correspondingly shaped curved washer is arranged, is provided concentrically in relation to the second bore 11 in the one clamping jaw 8 of the clamping body 6. The curved washer 22 has a conical depression 23 matched to the conical transition area 19 of the clamping screw 12, wherein an edge 24 is formed in which a portion of the bore 15 extends.

In the course of the fixation of the implant, the pedicle screws 1 as well as the connecting rod 2 are simultaneously clamped by screwing a nut 26 on the screw thread 25 of the clamping screw 12.

In accordance with the embodiment of FIGS. 6 and 7, the clamping screw 27 has two parallel extending flattened areas 28, which correspond with flattened areas, not shown in more detail, in the curved washer 29—with the elongated hole matching the flattened area 28—and of the second bore 11. By means of this step it is intended to prevent the twisting of the clamping screw 27, or respectively to assure that the curved washer turns along in the released state, so that it is assured in every position that the connecting rod does not slip out of the depressions and would therefore be in a position to be twisted.

The clamping devices in accordance with the invention will be described in what follows, making reference to FIGS. 11 to 18.

Figure 11:
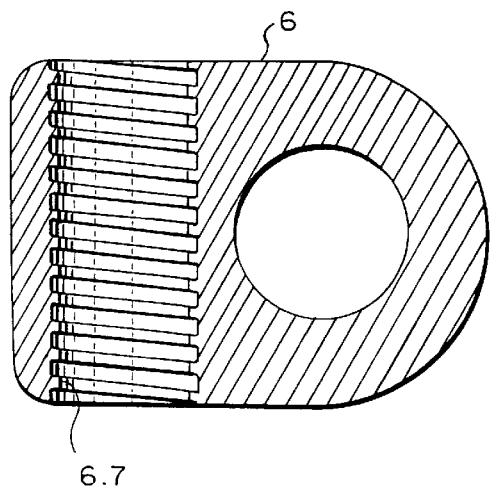
FIG. 11 represents a clamping body in accordance with the invention, with set-back areas at the inner surface of the recess intended for the implant pin in a first embodiment.

FIG. 11 shows a clamping body 6 with set-back areas on the originally cylindrical inner surface of the recess, or respectively bore 7, which are constituted by a helically-shaped recess 6.7. In actuality this is a single continuous set-back area. Set-back areas are formed in a similar manner on the clamping element 6 in accordance with FIG. 12 by circumferential grooves or channels 6.8.

The set-back area, or respectively areas in the form of a helical line, or respectively in the form of several channels or grooves, can also be arranged in a manner not shown on the implant pin 1 instead of the clamping element 6.

Figure 12:
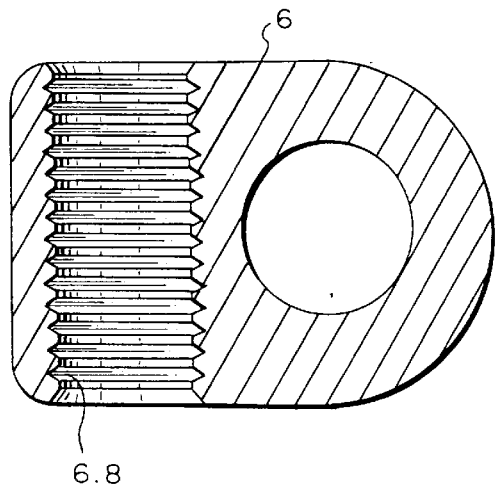
FIG. 12 represents a clamping body in accordance with the invention, with set-back areas at the inner surface of the recess intended for the implant pin in a second embodiment.
Figure 13:
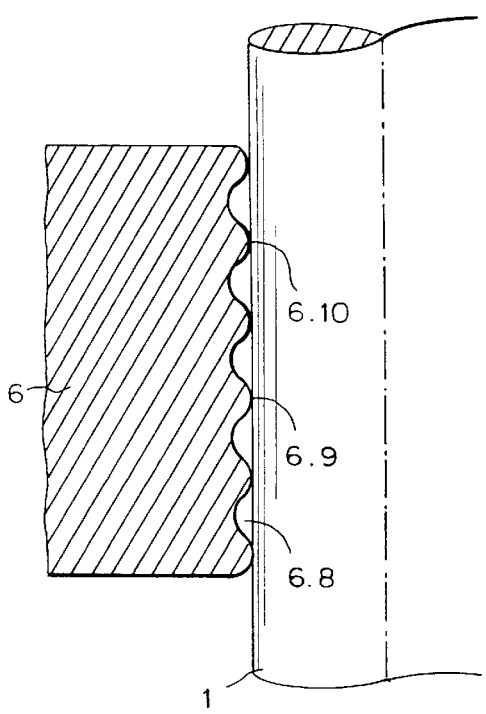
FIG. 13 shows sections of a contour, wavy in a sectional view, of the recess intended for the implant pin.
Figure 14:
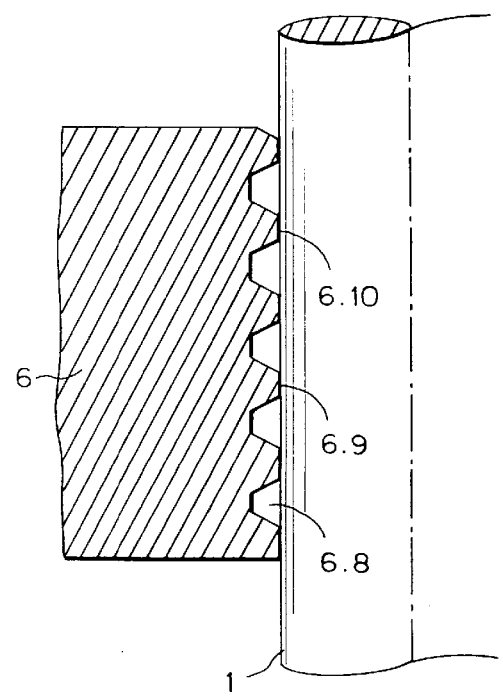
FIG. 14 shows a contour of the recesses intended for the implant pin, which in a sectional view forms a sequence of trapezoids.
Figure 15:
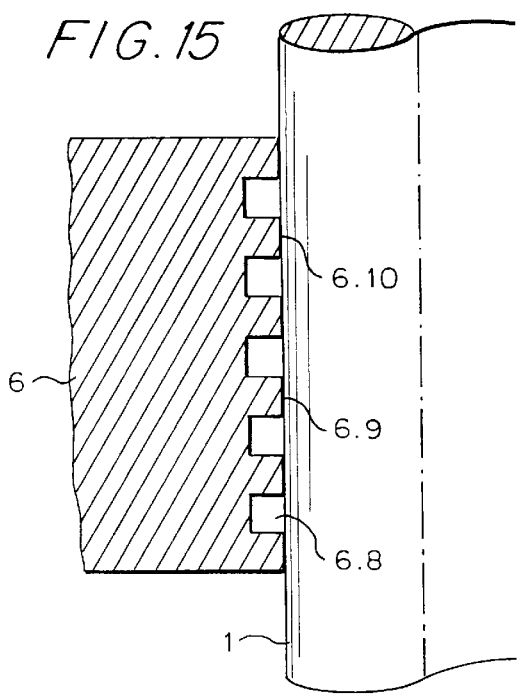
FIG. 15 shows a contour of the recesses intended for the implant pin, which in a sectional view forms a sequence of rectangles.
Figure 16:
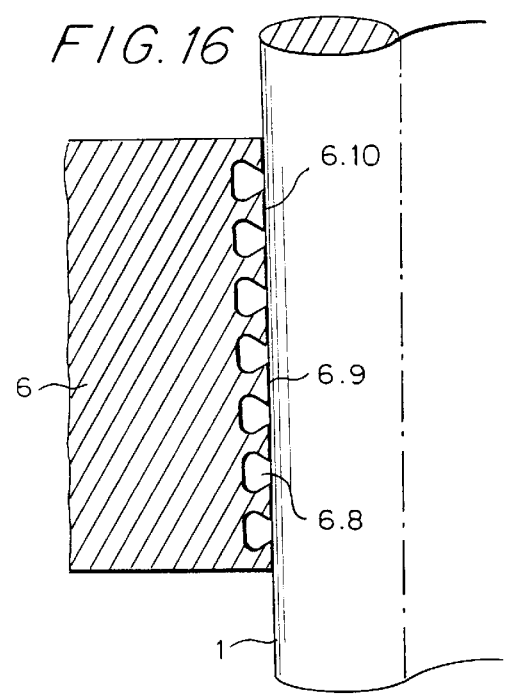
FIG. 16 shows a contour of the recesses intended for the implant pin, which in a sectional view forms a sequence of dovetails.

FIGS. 13 to 16 show various embodiment options for the contours of channel-like recesses 6.8, which constitute the set-back areas of the recess 7 on a clamping body in accordance with FIG. 12.

By the presence of the set-back areas 6.8, the mutual contact between the cylindrical implant pin 1 and the surface bordering the recess 7 is limited to the culmination surfaces 6.10 of the protrusions 6.9 projecting into the interior of the bore 7. Miscellaneous forces which are transmitted between the implant pin 1 and the clamping body 6 therefore can only take place via these culmination surfaces 6.10. The protrusions 6.9 are minimally elastically deformed by such forces, because of which the creation of material fatigue and wear is reduced.

Figure 17:
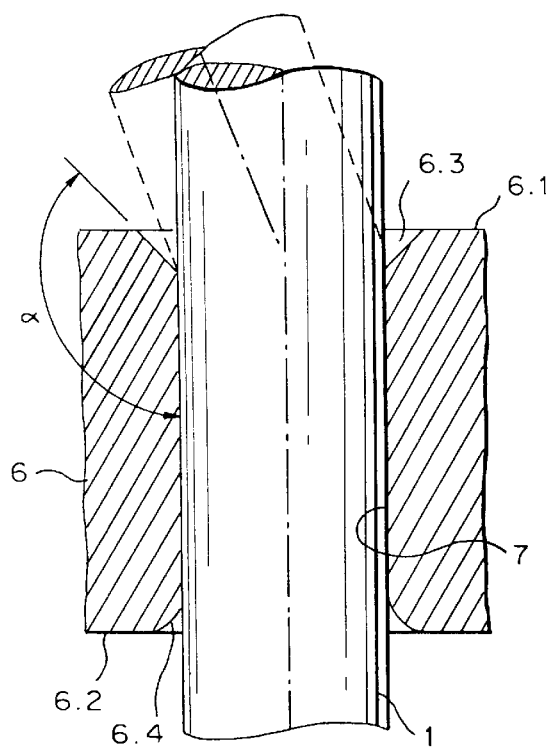
FIG. 17 represents sections of a clamping arrangement in accordance with the invention with a clamping body, an implant pin and with relief recesses on the clamping body.

FIG. 17 shows the clamping body 6 with the first bore, or respectively recess 7 and the implant pin 1. At the transition of the recess 7 with its outer surface 6.1 located at the top, the clamping body 6 has a relief recess in the shape of a broken circumferential edge 6.3, which makes a transition via a small curve into the wall of the recess 7. The clamping body 6 is also provided with a relief recess at the transition between the wall of the recess 7 to the outer surface 6.2 located at the bottom, which in this case is in the shape of a curve 6.4.

Figure 18:
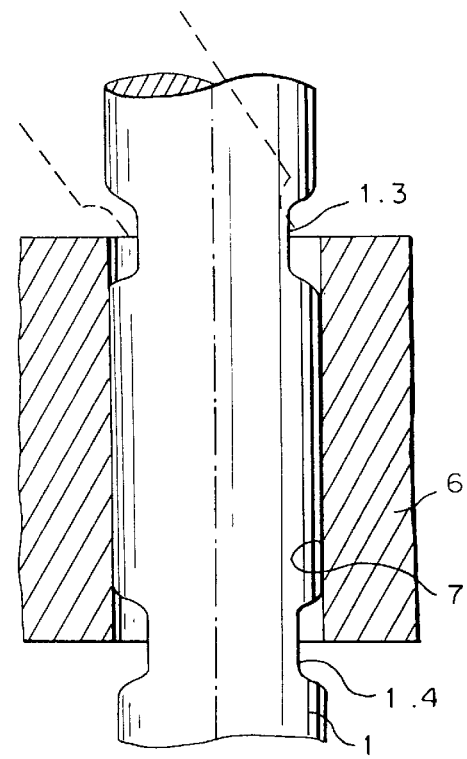
FIG. 18 represents sections of a clamping arrangement in accordance with the invention with a clamping body, an implant pin and with relief recesses on the implant body.

In the exemplary embodiment of FIG. 18, instead of the clamping body 6 the implant pin 1 is provided with one relief recess each in the form of a circumferential groove or channel 1.3, or respectively 1.4 in the area of its upper exit cross section 1.1 and its lower exit cross section 1.2.

The position an implant pin 1 would take if bent above the clamping body 6 is indicated by dashed lines both in FIG. 17 and FIG. 18, however with the bending angle greatly exaggerated. It can be clearly seen that with an arrangement in accordance with FIG. 18, as a result of the relief recesses 1.3, 1.4, neither pressure nor a nicking effect can be exerted on the implant pin 1 by the edge 6.0 of the clamping body 6. With the arrangement of FIG. 17 a nicking effect exists at the top, unless an additional rounding is provided, however it is defused in that possibly the nicking edge 6.9 does not form a right angle, as would be the case without a break in the edge, or respectively inclination 6.3, but an obtuse angle.

In an arrangement in accordance with FIG. 17, a nicking effect at the bottom is impossible because of the rounding 6.4.

FIGS. 13 to 16 show that with a suitable arrangement and size of the channels forming the set-back areas 6.3, the channels are also used as relief recesses in the area of the end cross sections 6.1, 6.2 of the clamping body 6.

It should further be mentioned that with fixation devices with clamping arrangements in accordance with the invention the number of load changes up to a break, which are a measure of the service life, lies in the range of twice that of fixation devices in accordance with Swiss Patent Application 00186/96 mentioned several times, this was also determined in a test arrangement. In spite of the increased service life, the total amount of rubbed off particles does not increase, which indicates that the amount of rubbed off particles is reduced over time.

The clamping arrangements described above constitute only a small selection of the clamping arrangements which are possible within the scope of the invention.

What is claimed is:

1. A clamping arrangement (1, 6) for an orthopedic fixation device, having a cylindrical implant pin (1) which can be fixed in place in a bone, and a clamping body (6), which has a cylindrical recess (7), connecting two oppositely located exterior surfaces (6.1, 6.2) of the clamping body (6) and receives the cylindrical implant pin (1), and a slit starting at the cylindrical recess (7), whose imagined extension contains the longitudinal axis of the cylindrical recess (7) and by means of which two resilient clamping jaws (8, 9) are formed on the clamping body (6) which, when clamped together, fastens the cylindrical implant pin (1) on the clamping body (6), wherein, one of two facing surfaces of the cylindrical recess (7) of the clamping body (6) and the cylindrical implant pin (1) has set-back areas which do not engage another of the two facing surfaces (6.7, 6.8) when the two facing surfaces abut along a common interface, wherein the set-back areas are constituted by a helical-like recess (6.7).

2. The clamping arrangement (1, 6) in accordance with claim 1, wherein in a sectional view through the longitudinal axis of the cylindrical recess (7) of the cylindrical implant pin (1), each set-back area forms a wave-like, trapezoid-like, rectangular or dovetail-like contour, with rounded edges and corners.

3. In an orthopedic fixation device comprising a clamping arrangement, the improvement wherein said clamping arrangement is in accordance with claim 2.

4. In an orthopedic fixation device comprising a clamping arrangement, the improvement wherein said clamping arrangement is in accordance with claim 1.

5. The clamping arrangement (1, 6) in accordance with claim 1, wherein the surface having the set-back areas is the wall of the cylindrical recess (7) of the clamping body (6).

6. In an orthopedic fixation device comprising a clamping arrangement, the improvement wherein said clamping arrangement is in accordance with claim 5.

7. The clamping arrangement (1, 6) in accordance with claim 1, wherein the surface having the set-back areas is the outer surface of the cylindrical implant pin (1).

8. In an orthopedic fixation device comprising a clamping arrangement, the improvement wherein said clamping arrangement is in accordance with claim 7.

9. The clamping arrangement (1, 6) in accordance with claim 1, wherein each set back area of said set back areas has a substantially identical cross-sectional form to each other.

10. In an orthopedic fixation device comprising a clamping arrangement, the improvement wherein said clamping arrangement is in accordance with claim 9.

11. A clamping arrangement (1, 6) for an orthopedic fixation device, having a cylindrical implant pin (1) which can be fixed in place in a bone, and a clamping body (6), which has a cylindrical recess (7), connecting two oppositely located exterior surfaces (6.1, 6.2) of the clamping body (6) and receives the cylindrical implant pin (1), and a slit starting at the cylindrical recess (7), whose imagined extension contains the longitudinal axis of the cylindrical recess (7) and by means of which two resilient clamping jaws (8, 9) are formed on the clamping body (6) which, when clamped together, fastens the cylindrical implant pin (1) on the clamping body (6), wherein, one of two facing surfaces of the cylindrical recess (7) of the clamping body (6) and the cylindrical implant pin (1) has set-back areas which do not engage another of the two facing surfaces (6.7, 6.8) when the two facing surfaces abut along a common interface, wherein the set-back areas are constituted by a plurality of channels (6.8) which extend perpendicularly with the longitudinal axis of the cylindrical recess (7), or of the cylindrical implant pin (1).

12. In an orthopedic fixation device comprising a clamping arrangement, the improvement wherein said clamping arrangement is in accordance with claim 11.

13. The clamping arrangement (1, 6) in accordance with claim 11 wherein, the surface having the set-back areas is the wall of the cylindrical recess (7) of the clamping body (6).

14. In an orthopedic fixation device comprising a clamping arrangement, the improvement wherein said clamping arrangement is in accordance with claim 13.

15. In an orthopedic fixation device comprising a clamping arrangement, the improvement wherein said clamping arrangement is in accordance with claim 13.

16. The clamping arrangement (1, 6) in accordance with claim 11 wherein, the surface having the set-back areas is the outer surface of the cylindrical implant pin (1).

17. In an orthopedic fixation device comprising a clamping arrangement, the improvement wherein said clamping arrangement is in accordance with claim 16.

18. In an orthopedic fixation device comprising a clamping arrangement, the improvement wherein said clamping arrangement is in accordance with claim 16.

19. The clamping arrangement (1, 6) in accordance with claim 11 wherein, in a sectional view through the longitudinal axis of the cylindrical recess (7), or of the cylindrical implant pin (1), each set-back area forms a wave-like, trapezoid-like, rectangular or dovetail-like contour, with rounded edges and corners.

20. In an orthopedic fixation device comprising a clamping arrangement, the improvement wherein said clamping arrangement is in accordance with claim 19.

21. In an orthopedic fixation device comprising a clamping arrangement, the improvement wherein said clamping arrangement is in accordance with claim 19.

22. The clamping arrangement (1, 6) in accordance with claim 11 wherein, each set-back area of said set back areas has a substantially identical cross-sectional form to each other.

* * * * *